| United States Patent [19] | [11] Patent Number: 4,897,086 |
| Blain et al. | [45] Date of Patent: Jan. 30, 1990 |

[54] LUBRICANT AND FUEL COMPOSITIONS CONTAINING REACTION PRODUCTS OF POLYALKENYL SUCCINIMIDES, ALDEHYDES, AND TRIAZOLES

[75] Inventors: David A. Blain, Morrisville, Pa.; Angeline B. Cardis, Florence, N.J.; Sylvia S. McGonigle, Chadds Ford, Pa.

[73] Assignee: Mobil Oil Corporation, New York, N.Y.

[21] Appl. No.: 290,405

[22] Filed: Dec. 29, 1988

[51] Int. Cl.$^4$ ............................ C10L 1/18; C10L 1/22
[52] U.S. Cl. .............................................. 44/53; 44/63; 44/64; 548/269; 548/546; 548/547
[58] Field of Search ............... 44/63, 64, 53; 548/546, 548/547, 269

[56] References Cited

U.S. PATENT DOCUMENTS

| 3,791,803 | 2/1974 | Andress, Jr. et al. | 44/62 |
| 4,153,564 | 5/1979 | Chibrik | 44/63 |
| 4,212,754 | 7/1980 | Chibrik | 44/63 |
| 4,263,015 | 4/1981 | Sung et al. | 44/63 |
| 4,282,007 | 8/1981 | Sung | 44/63 |
| 4,464,276 | 8/1984 | Sung et al. | 548/269 |

*Primary Examiner*—William R. Dixon, Jr.
*Assistant Examiner*—Ellen M. McAvoy
*Attorney, Agent, or Firm*—Alexander J. McKillop; Charles J. Speciale; Howard M. Flournoy

[57] ABSTRACT

Disclosed is an additive for liquid hydrocarbon fuel composition, particularly diesel fuels. The additive composition is the reaction product of polyalkenyl-substituted succinimides, aldehydes, and triazoles. It also finds use in lubricant compositions.

22 Claims, No Drawings

LUBRICANT AND FUEL COMPOSITIONS CONTAINING REACTION PRODUCTS OF POLYALKENYL SUCCINIMIDES, ALDEHYDES, AND TRIAZOLES

NATURE OF THE INVENTION

This invention relates to lubricant and fuel compositions. More specifically it is concerned with the reaction products of polyalkenyl-substituted succinimides aldehydes, and triazoles useful as multifunctional detergents, dispersants, and antioxidants in lubricant compositions and in fuel compositions including liquid hydrocarbons, diesel fuel and oxygenated fuels such as alcohols and ether compounds.

BACKGROUND OF THE INVENTION

Impurities occurring in diesel fuels can produce soluble and insoluble materials which are responsible for gum deposits and discoloration of the fuel. Other impurities may result from handling, corrosion of storage vessels and may even be introduced by the refiner to prevent or solve other problems with the fuel such as oxidation, rust promotion, etc. The end result can be the formation of deposits in the diesel engine, particularly with respect to the fuel injectors. The eventual result is poor engine performance with increased noise, starting problems and decreased power output and fuel economy. A primary purpose of this invention accordingly is to provide an additive for fuels, particularly diesel fuels, which will help reduce engine deposits. Another purpose of this invention is to provide an additive which will improve the stability and cleanliness of lube oil compositions.

SUMMARY OF THE INVENTION

Briefly stated this invention comprises in one aspect a lubricant composition and in another aspect a liquid hydrocarbon fuel composition containing in addition to a major portion of a lubricant or hydrocarbon fuel a minor portion of an additive composition which is the reaction product of a polyalkenyl-substituted succinimide, an aldehyde, and a triazole. The invention further comprises the method for making the additive composition. The additive itself is a multifunctional additive in that, in addition to its detergent/dispersant activity, it operates as an anti-rust, anti-wear, and friction reducing agent.

DESCRIPTION OF THE INVENTION

As indicated above the this invention comprises the lubricant composition or the liquid hydrocarbon fuel composition containing the reaction product of a polyalkenyl-substituted succinimide, an aldehyde, and a triazole. The substituted or modified succinimides have the structural formula:

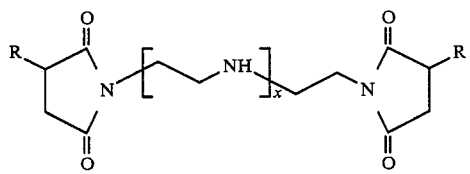

where R is an alkyl or alkenyl group of 9 to 150 carbon atoms, and X is 1 to 4. Although polyisobutylene is a particularly preferred substituent, other substituents can be, but are not limited to, polypropylene, other polyolefins, as well as monomeric olefins.

The triazoles have the structural formula:

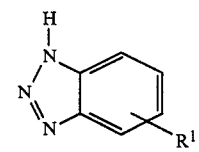

where $R^1$ is hydrogen or an alkyl, aryl, arylalkyl, or alkylaryl group of 1 to 12 carbon atoms. A preferred triazole is tolyltriazole. The aldehyde used in preparing the reaction product can be alkyl, aryl, alkylaryl, or arylalkyl containing 1 to 12 carbon atoms. Also included is formaldehyde, the paraformaldehyde form being more preferred.

The polyalkenyl-substituted succinimide, aldehyde, and triazole are reacted in a mole ratio of succinimide to aldehyde to triazole respectively of between 1 to 0.1 to 0.1 and 1 to 4 to 4, preferably at a temperature of 100° C. to 200° C. at ambient pressure. If desired the reaction can be conducted in a carrier solvent such as xylene or toluene and in a non-reactive atmosphere. After reaction is complete the reaction mass is treated to remove any solvent or water of reaction. The resulting product is the desired additive product. Although we do not wish to be bound by it, it is thought that the reaction product may have the general formula:

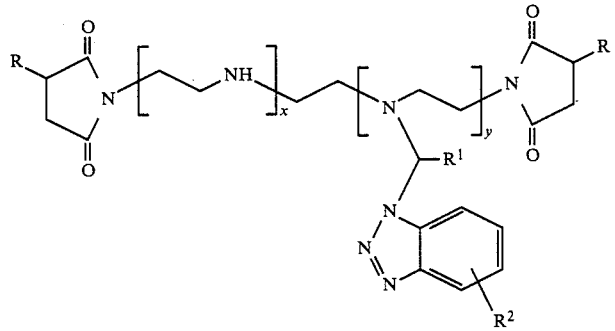

where R is an alkyl or alkenyl group of 9 to 150 carbon atoms, $R^1$ and $R^2$ are each hydrogen or an alkyl, aryl, arylalkyl, alkylarlyl group of 1 to 12 carbon atoms, y is greater than O, and x +y is equal to 1 to 4.

In preparing a fuel composition the additive is added at a rate of between 25 and 500 pounds of additive per 1000 barrels of fuel. The liquid fuel can be a liquid hydrocarbon fuel or an oxygenated fuel or mixtures thereof. Liquid hydrocarbon fuels include gasoline, fuel oils, diesel oils, and alcohol fuels including methyl and ethyl alcohols and ethers.

It is to be understood that the liquid fuel compositions described herein can also contain other materials. For example, corrosion inhibitors, co-antioxidants, and the like can be used.

In preparing a lubricant composition the additive is added to the base lubricating oil stock in a concentration of between 0.1 and 10 percent by weight of the total composition. In general, the mineral oils, both paraffinic, naphthenic and mixtures thereof, employed as a lubricating oil or as the grease vehicle, can be of any suitable lubricating viscosity range, as for example, from about 45 SSU at 100° F. to about 6000 SSU at 100° F., and preferably from about 50 to about 250 SSU at 210° F. These oils may have viscosity indexes ranging to 100 or higher. Viscosity indexes from about 70 to about 95 are preferred. The average molecular weight of these oils can range from about 250 to about 800.

Where the lubricant is employed as a grease, the lubricating oil is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt and dissolve when used at the required temperature within a particular enviroment; however, in all other respects, any material which is normally employed for thickening or gelling hydrocarbon fluids for forming grease an be used in preparing the aforementioned improved grease in accordance with the present invention.

In instances where synthetic oils, or synthetic oils employed as the vehicle for the grease, are desired in preference to minerals oils, or in preference to mixtures of mineral and synthetic oils, various synthetic oils may be utilized successfully. Typical synthetic oil vehicles include polyisobutylenes, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl) ether, and phenoxy phenylethers.

It is to be understood that the grease compositions described herein can also contain other materials, eg, corrosion inhibitors, extreme pressure agents, viscosity index improvers, antioxidants, antiwear agents and the like can be used. These include, but are not limited to, phenates, sulfonates, succinimides, zinc dialkyl or diaryl dithiophosphates, and the like.

EXAMPLE 1

A weight of 10.7 grams (0.08 mole) of tolyltriazole, 236.2 grams (0.08 mole) of a polyisobutenyl succinimide (made from tetraethylene pentamine and a polyisobutenyl succinic anhydride which is the reaction product of maleic anhydride and a 920 MW polyisobutylene), and 200 ml of toluene were charged to a 500 ml reactor equipped with an $N_2$ inlet, mechanical stirrer, thermometer, and Dean Stark trap. The temperature was raised to 70° C. and 1.3 grams (0.04 mole) paraformaldehyde was added. After a half hour at this temperature another 1.3 grams portion of paraformaldehyde was added. The reaction was brought to reflux. After 1.5 hours, 1.6 ml of water had been collected. The reaction temperature was increased to 150° C. by removing solvent through the Dean Stark trap. It was kept at this temperature for one hour during which time residual solvent was removed under a stream of $N_2$. The viscous product was filtered through a bed of hot celite.

EXAMPLE 2

A weight of 8.0 grams (0.06 mole) of tolyltriazole, 87.7 grams (0.03 mole) of a polyisobutenyl succinimide (made from tetraethylene pentamine and a polyisobutenyl succinic anhydride which is the reaction product of maleic anhydride and a 920 MW polyisobutylene), and 100 ml of toluene were charged to a 500 ml reactor equipped with an $N_2$ inlet, mechanical stirrer, thermometer, and Dean Stark trap. The temperature was raised to 70° C. and 1.9 grams (0.06 mole) paraformaldehyde was added. The reaction was brought to reflux. After 4.0 hours, 1.1 ml of water had been collected. The solvent was removed via rotary evaportion, first under house vacuum (250–300 mm Hg) and the with a vacuum pump (1–3 mm Hg). The viscous product was filtered through a bed of hot celite.

EXAMPLE 3

The procedure from Example 2 was followed with the following exception: The ratio of tolyltriazole to succinimide to paraformaldehyde was changed to 3 to 1 to 3.

EXAMPLE 4

The procedure from Example 2 was followed with the following exceptions: The ratio of tolyltriazole to succinimide to paraformaldehyde was changed to 1 to 1 to 1 and the polyiosbutenyl succinimide was made from a 460 MW polyisobutylene.

EXAMPLE 5

The procedure from Example 4 was followed with the following exception: The ratio of tolyltriazole to succinimide to paraformaldehyde was changed to 0.1 to 1 to 0.1.

FUEL TESTS

The product obtained in Example 4 above was blended into diesel fuel in a ratio of 50 lb/1000 barrels and the fuel was tested for color and oxidative stability using a 90 minute stability test conducted at 300° F. Fuel (ASTM D 1500) color was determined using a colorimeter. Sediment formation was determined by vacuum filtration of the fuel through two Whatman #1, 4.25 cm filters. Then, the appearance of the top filter is rated by comparing it to the standard set of filter pads, numbered 1 to 20, where a rating of 20 indicates poor stability (more sediment formation). Test results are as follows.

| Fuel | Color Initial | Color Aged | Filter Rating Initial | Filter Rating Aged |
|---|---|---|---|---|
| Base Diesel Fuel | 4.5 | 7.0 | 5 | 16 |
| Base + 100 lb of Commercial Detergent Additive Package Containing an Anti-Rust Additive per 1000 Barrels of Diesel Fuel | 4.5 | 5.5 | 5 | 2 |
| Base + 50 lb of additive of Example 4 per 1000 Barrels of Diesel Fuel | 4.5 | 5.0 | 5 | 2 |

The product of this invention was also tested for its ability to keep fuel injectors clean in a Peugot 505 STD equipped with standard pintle injectors. To accelerate injector coking, the vehicle was operated for 6 hours under sever steady-state conditions of high speed and load. The extent of injector deposits was assessed based on the air flow characteristics of the nozzle before and after tests. Performance comparisons are based on percent air flow restriction versus new injectors at 0.1 mm needle lift.

| Fuel | % Restriction |
|---|---|
| Base | 51 |
| Base + 100 lb/MB Commercial Detergent Additive Package | 23 |
| Base + 50 lb/MB Example 4 | 5 |

From these results it is readily apparent that the product of this invention not only imparts color stability and reduces sediment formation but that it is effective in keeping fuel injectors clean.

EXAMPLE 6

The procedure from Example 2 was followed with the following exceptions: Benzaldehyde was substituted for paraformaldehyde and the ratio of tolyltriazole to succinimide to benzaldehyde was changed to 1 to 1 to 1.

EXAMPLE 7

The procedure from Example 2 was followed with the folowing exceptions: 2-ethylhexanal was substituted for paraformaldehyde and the ratio of tolyltrizole to succinimide to 2-ethylhexanal was changed to 1 to 1 to 1.

EXAMPLE 8

The procedure from Example 2 was followed with the following exceptions: Salicylaldehyde was substituted for paraformaldehyde and the ratio of tolyltriazole to succinimide to salicylaldehyde was changed to 1 to 1 to 1.

EXAMPLE 9

The procedure from Example 6 was followed with the following exceptions: The ratio of tolyltrizole to succinimide to benzaldehyde was changed to 2 to 1 to 2.

EXAMPLE 10

The procedure from Example 7 was followed with the following exceptions: The ratio of tolyltrizole to succinimide to 2-ethylhexanal was changed to 2 to 1 to 2.

EXAMPLE 11

The procedure from Example 8 was followed with the following exceptions: The ratio of tolyltrizole to succinimide to salicylaldehyde was changed to 2 to 1 to 2.

The additive described above were evaluated to show their antioxidant capabilities in a concentration of 4 percent in a fully formulated marine diesel lubricant. Results were as follows.

| B-10 Catalytic Oxidation Test, 375° F., 24 Hours | | |
|---|---|---|
| Additive | ΔNN | % ΔKV |
| None | 4.1 | 72.9 |
| Commercial Dispersant | 5.2 | 77.1 |
| Example 2 | 5.2 | 47.8 |
| Example 5 | 5.1 | 62.4 |
| Example 6 | 3.7 | 38.1 |
| Example 7 | 4.7 | 45.3 |
| Example 8 | 4.1 | 34.7 |
| Example 9 | 4.9 | 56.3 |
| Example 10 | 4.4 | 47.7 |

We claim:

1. The reaction product obtained by reacting a polyalkenyl-substituted succinimide having the structural formula:

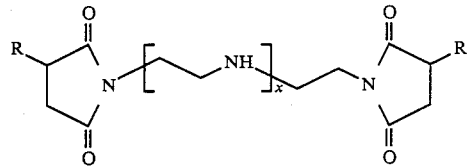

where R is an alkyl or alkenyl group of 9 to 150 carbon atoms, and x is 1 to 4 with a triazole having the structural formula:

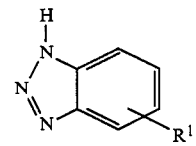

where $R^1$ is hydrogen or an alkyl, aryl, arylalkyl, or alkylaryl group of 1 to 12 arbon atoms and an aldehyde in a molar ratio of succinimide to aldehyde to triazole respectively of between about 1 to 0.1 to 0.1 and about 1 to 4 to 4 at a temperature of about 100° C. to about 200° C. at ambient pressure.

2. The reaction product of claim 1 wherein the polyalkenyl-substituted succinimide is a polyisobutenyl succinimide.

3. A method for making a fuel composition comprising adding to a liquid hydrocarbon fuel or liquid oxygenated fuel or mixtures thereof between about 25 and about 500 pounds per 1000 barrels of fuel of the reaction product of claim 2.

4. The reaction product of claim 1 wherein the triazole is tolyltriazole.

5. A method for making a fuel composition comprising adding to a liquid hydrocarbon fuel or liquid oxygenated fuel or mixtures thereof between about 25 and about 500 pounds per 1000 barrels of fuel of the reaction product of claim 4.

6. The reaction product of claim 1 wherein the aldehyde is selected from the group consisting of formaldehyde, paraformaldehyde, benzaldehyde, salicylaldehyde, and 2-ethylhexanal.

7. A method for making a fuel composition comprising adding to a liquid hydrocarbon fuel or liquid oxygenated fuel or mixtures thereof between about 25 and about 500 pounds per 1000 barrels of fuel of the reaction product of claim 6.

8. The reaction product of claim 1 wherein the reaction product has the structural formula:

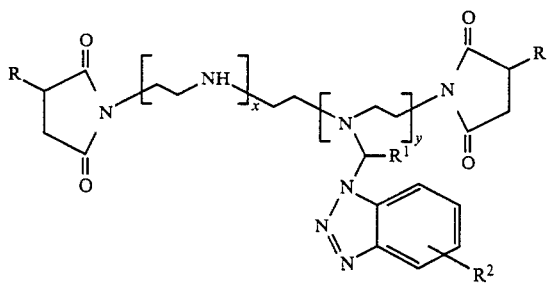

where R is an alkyl or alkenyl group of 9 to 150 carbon atoms, , $R^1$ and $R^2$ are each hydrogen or an alkyl, aryl, arylalkyl, alkylaryl group of 1 to 12 carbon atoms, y is greater than 0, and x +y is equal to 1 to 4.

9. A method for making a fuel composition comprising adding to a liquid hydrocarbon fuel or liquid oxygenated fuel or mixtures thereof between about 25 and about 500 pounds per 1000 barrels of fuel of the reaction product of claim 8.

10. The reaction product of claim 1 wherein the reaction is conducted in a carrier solvent selected from the group consisting of xylene and toluene.

11. A method for making a fuel composition comprising adding to a liquid hydrocarbon fuel or liquid oxygenated fuel or mixtures thereof between about 25 and about 500 pounds per 1000 barrels of fuel of the reaction product of claim 1.

12. A liquid fuel composition comprising a major proportion of a fuel and between about 25 and about 500 pounds per 1000 barrels of fuel of a reaction product obtained by reacting a polyalkenyl-substituted succinimide having the structural formula:

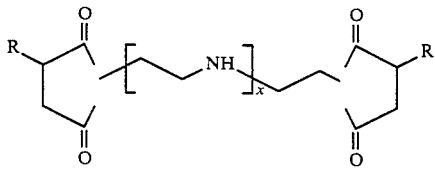

where R is an alkyl or alkenyl group of 9 to 150 carbon atoms with a triazole having the structural formula:

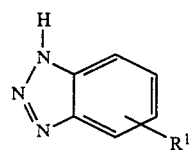

where $R^1$ is hydrogen or an alkyl, aryl, arylalkyl, or alkylaryl group of 1 to 12 carbon atoms and an aldehyde in a molar ratio of succinimide to aldehyde to triazole respectively of between about 1 to 0.1 to 0.1 and about 1 to 4 to 4 at a temperature of about 100° C. to about 200° C. at ambient pressure.

13. The composition of claim 12 wherein the polyalkenyl-substituted succinimide is a polyisobutenyl succinimide.

14. The composition of claim 12 wherein the triazole is tolyltriazole.

15. The composition of claim 12 wherein the aldehyde is formaldehyde.

16. The composition of claim 12 wherein the reaction product has the structural formula:

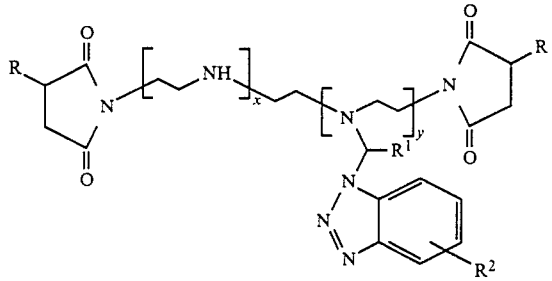

where R is an alkyl or alkenyl group of 9 to 150 carbon atoms, , $R^1$ and $R^2$ are each hydrogen or an alkyl, aryl, arylalkyl, alkylaryl group of 1 to 12 carbon atoms, y is greater than 0, and x +y is equal to 1 to 4.

17. The composition of claim 12 wherein the reaction is conducted in a carrier solvent selected from the group consisting of xylene and toluene.

18. The composition of claim 12 wherein the concentration of said reaction product in said fuel is between about 25 pounds and about 500 pounds per 1000 barrels of fuel.

19. The composition of claim 12 wherein the fuel is a liquid hydrocarbon.

20. The composition of claim 12 wherein the fuel is an alcohol or ether.

21. The composition of claim 12 wherein the fuel is diesel fuel.

22. The composition of claim 12 wherein the fuel is a mixture of liquid hydrocarbons and alcohol and/or ether.

* * * * *